US011767304B2

(12) United States Patent
Xu et al.

(10) Patent No.: US 11,767,304 B2
(45) Date of Patent: Sep. 26, 2023

(54) SYSTEM AND METHOD FOR CONTINUOUSLY PREPARING FURFURAL USING LIGNOCELLULOSIC RAW MATERIAL

(71) Applicant: ECO Environmental Energy Research Institute Limited, Hong Kong (CN)

(72) Inventors: Bin Xu, Hong Kong (CN); Kam Shing Siu, Hong Kong (CN); Junde Lu, Hong Kong (CN); Connie Hiu Ying Chow, Hong Kong (CN)

(73) Assignee: ECO ENVIRONMENTAL ENERGY RESEARCH INSTITUTE LIMITED, Hong Kong (CN)

( * ) Notice: Subject to any disclaimer, the term of this patent is extended or adjusted under 35 U.S.C. 154(b) by 550 days.

(21) Appl. No.: 16/894,672

(22) Filed: Jun. 5, 2020

(65) Prior Publication Data

US 2020/0369637 A1 Nov. 26, 2020

Related U.S. Application Data

(63) Continuation of application No. PCT/CN2018/117649, filed on Nov. 27, 2018.

(30) Foreign Application Priority Data

Dec. 6, 2017 (CN) .......................... 201711277935.4
Dec. 6, 2017 (CN) .......................... 201721685502.8

(51) Int. Cl.
*C07D 307/50* (2006.01)
*B01D 3/14* (2006.01)
*B01D 5/00* (2006.01)

(52) U.S. Cl.
CPC ........... *C07D 307/50* (2013.01); *B01D 3/148* (2013.01); *B01D 5/006* (2013.01)

(58) Field of Classification Search
None
See application file for complete search history.

(56) References Cited

U.S. PATENT DOCUMENTS

| 11,319,499 B1 * | 5/2022 | Matson | C07C 51/00 |
| 11,358,943 B2 * | 6/2022 | Liu | C07D 307/50 |
| 2015/0140616 A1 * | 5/2015 | Binder | C08H 8/00 |
| | | | 435/126 |
| 2021/0206737 A1 * | 7/2021 | Liu | C07D 307/50 |

FOREIGN PATENT DOCUMENTS

| CN | 1824379 A | 8/2006 |
| CN | 101108838 A | 1/2008 |
| CN | 101130532 A | 2/2008 |
| CN | 102596384 A | 7/2012 |
| CN | 103130756 A | 6/2013 |
| CN | 107235939 A | 10/2017 |
| CN | 107827847 A | 3/2018 |
| CN | 207877625 U | 9/2018 |
| GB | 774809 | 5/1957 |
| WO | 2012057625 A2 | 5/2012 |

OTHER PUBLICATIONS

International Search Report and Written Opinion dated Mar. 6, 2019 in connection with International Application No. PCT/CN2018/117648, 16 pages.
First Office Action dated Sep. 2, 2020 in connection with Chinese Application No. 201711277935.4, 8 pages.
China Academic Journal Electronic Publishing House, "Sodium acetate recovery technology in furfural production", http://www.cnki.net, 1994-2020, 2 pages.
Extended European Search Report dated May 11, 2021 in connection with European Application No. 18885815.3, 9 pages.

* cited by examiner

*Primary Examiner* — Randy Boyer
(74) *Attorney, Agent, or Firm* — Baker & McKenzie LLP (57) ABSTRACT

The present invention discloses a system and a method for continuously preparing furfural using lignocellulosic raw material. The system comprises an acid solution output unit, a raw material mixing unit, a feeding unit, a main reaction unit, a discharging unit, a stripping reaction column, a separation unit, and a purification unit. The method comprises an acid solution output step, a raw material mixing step, a feeding step, a hydrolysis reaction step, a discharging step, a stripping reaction step, a separation step, and a purification step. The present invention is a genuine continuous production system, which achieves continuous acquisition of products in terms of time, reduces labor intensity, and improves production efficiency. The whole process has a reasonable design, high furfural yields and low unit energy consumption.

32 Claims, 2 Drawing Sheets

SYSTEM AND METHOD FOR CONTINUOUSLY PREPARING FURFURAL USING LIGNOCELLULOSIC RAW MATERIAL

CROSS-REFERENCE TO RELATED APPLICATIONS

This application is a continuation application of International Application No. PCT/CN2018/117649 filed Nov. 27, 2018, which claims priority to Chinese Application No. 201721685502.8 filed Dec. 6, 2017 and claims priority to Chinese Application No. 201711277935.4 filed Dec. 6, 2017, the contents of all of which are hereby expressly incorporated by reference in their entirety, including the contents and teachings of any references contained therein.

TECHNICAL FIELD

The present invention belongs to the technical field of furfural production, in particular to a technique for continuously preparing furfural with a two-step process.

BACKGROUND

Furfural (also known as furaldehyde) is an important chemical product and widely used in synthetic plastics, pharmaceuticals, pesticides and other industrial fields. The annual demand for furfural is enormous globally. The furfural can selectively extract unsaturated components from petroleum and vegetable oils, as well as aromatic components from lubricating oils and diesel oils. With the intensification of the energy crisis and environmental protection requirements, the use of renewable agricultural and forestry waste to produce high value-added furfural has received increasing attention.

At present, on the industrial scale, the sole method for obtaining furfural is still a hydrolysis method by taking corncob as a raw material. The furfural production technology can be further divided into a one-step method and a two-step method, depending on whether the pentosan hydrolysis and the dehydration/cyclization of the pentose monomer starting from corncob hemicellulose are carried out in the same reactor.

In the one-step method, the hemicellulose-containing raw material is placed into a hydrolysis pot. The hemicellulose is hydrolyzed to be pentose under a certain temperature and with acid catalysis, and the pentose is simultaneously dehydrated to form the furfural. The one-step method is widely used in the furfural industry because of its low investment in equipments and simple operation. However, the one-step method could lead to low furfural yield, large vapor consumption and serious environmental pollution because the raw material are not heated uniformly.

The two-step method divides the hydrolysis reaction of hemicellulose and the dehydration reaction of pentose into two steps, which are respectively carried out in different equipments, and the reaction formula is as follows:

At present, domestically or internationally, the first step in the two-step method, the process of producing sugar from lignocellulosic raw materials is usually carried out by dilute acid hydrolysis. The existing acid hydrolysis devices are batch reactors, which have high labor intensity, low production efficiency, large area coverage and serious pollution. In addition, for existing reactor, due to the problems of acid solution only attaching to the surface of the material, heterogeneous mixing of the material and the acid solution, and heterogeneous heating of water vapor, the decomposition of the hydrolyzed sugar, more by-products, small sugar yield, and low sugar concentration would happen.

In the second step of the two-step method, i.e., the pentose dehydration/cyclization process, the furfural yield is low due to the decomposition reaction of the furfural itself and the polycondensation reaction of the reaction intermediate. Since developed countries such as Europe and the United States have already stopped furfural production, there are few researches and reports on furfural technology.

Therefore, the study on systems and methods for continuously producing furfural using lignocellulosic raw material has a positive significance for solving the abovementioned technical problems in the prior art.

SUMMARY

The present invention has been presented in view of the abovementioned problems in the prior art. The invention provides a system for continuously preparing furfural with lignocellulosic raw material and also a method for continuously preparing furfural with lignocellulosic raw material, which at least solves the problems of discontinuous reaction, low furfural yield and production efficiency, many reaction by-products, large labor intensity, high production cost, and serious environmental pollution and the like in the prior art. It can effectively enhance production efficiency and furfural yield, reduce labor intensity, and avoid the occurrence of side reactions as much as possible, with low unit energy consumption and environmental pollution and rational utilization of energy.

According to an aspect of the present invention, a system for continuously preparing furfural with lignocellulosic raw material is provided. The system comprises:
- an acid solution output unit for outputting a first acid solution and a second acid solution respectively;
- a raw material mixing unit connected to the acid solution output unit, for mixing the raw material with the first acid solution to form a mixture and continuously conveying the mixture;
- a feeding unit connected to the raw material mixing unit, for receiving the mixture, compressing the mixture and conveying the mixture outward;
- a main reaction unit connected to the feeding unit and the acid solution output unit, for receiving the mixture and the second acid solution respectively, and sufficiently stirring and mixing the mixture with the second acid solution under a pressure higher than a normal pressure to cause them to react;
- a discharging unit connected to the main reaction unit, for performing solid-liquid separation of a resultant obtained from the reaction and outputting an acid-containing pentose solution;
- a stripping reaction column comprising, at the top, a vapor outlet and a first raw material inlet, and at the bottom, a stripping vapor inlet and an acid solution outlet, wherein the first raw material inlet is for receiving an acid-containing pentose solution of a first temperature as a raw material from the discharging unit for performing a dehydration/cyclization reaction, the stripping vapor inlet is for receiving a stripping vapor of a second temperature; the vapor outlet is for providing a furfural-containing vapor obtained from the reaction, the acid solution outlet is for extracting acid solution from the bottom of the column;

a separation unit connected to the vapor outlet for neutralizing the acid in the furfural-containing vapor and separating the resulting salt from the furfural-containing vapor to provide a furfural-containing vapor with a reduced acid content; and a purification unit for purifying the resulting furfural.

According to another aspect of the present invention, a method for continuously preparing furfural using lignocellulosic raw material is provided. The method comprises:

an acid solution output step for outputting a first acid solution and a second acid solution respectively;

a raw material mixing step for mixing the raw material with the first acid solution to form a mixture;

a feeding step for compressing the mixture and conveying the mixture outward;

a hydrolysis reaction step for uniformly mixing the mixture with the second acid solution and causing them to perform a hydrolysis reaction at a pressure higher than a normal pressure;

a discharging step for performing solid-liquid separation of a resultant obtained from the hydrolysis reaction, in order to obtain a liquid as an acid-containing pentose solution;

a stripping reaction step, which is performed using a stripping reaction column, wherein the acid-containing pentose solution from the discharging step of a first temperature enters the stripping reaction column from the top; a stripping vapor of a second temperature enters the stripping reaction column from the bottom; the stripping vapor is in countercurrent contact with the pentose solution, which is subject to a dehydration/cyclization reaction so as to obtain a furfural-containing vapor and an acid solution;

a separation step, wherein the furfural-containing vapor is neutralized and the resulting salt is separated from the furfural-containing vapor to provide a furfural-containing vapor with a reduced acid content; and a purification step, wherein the resulting furfural is purified.

The present invention provides a continuous production system in a real sense, and achieves continuous acquisition of the product in terms of time, which reduces labor intensity and improves production efficiency. Moreover, the hydrolysis reaction of the lignocellulosic raw material occurs only in the main reaction unit, which reduces the formation of by-products, and the sugar obtained from the reaction can be discharged timely, thereby improving sugar yield and sugar concentration. During the process of preparing furfural with pentose, a liquid inorganic acid can be used as a catalyst in the stripping reaction column, with strong catalytic ability and low reaction temperature. The stripping reaction column can also treat low concentration sugar solution, without need to condense the sugar solution and thereby simplify the process. The present invention adopts a vapor counterflow stripping reaction process, into which no extractant is added, and the acid-containing pentose solution contacts the vapor from top to bottom. While the furfural is generated with the dehydration/cyclization reaction, the furfural as generated is brought out by the vapor simultaneously, thus avoiding the side reaction of furfural due to being in a liquid acidic environment for a long time. The bottom of the stripping reaction column of the present invention is free of a reboiler, and the top thereof is free of a reflux unit. Since the pentose-containing solution usually contains salts and other sugar impurities, the heat exchange in the reboiler in an acidic environment easily causes the surface of the reboiler to coke and thereby the reaction could not proceed continuously, while heating with vapor directly stripping avoids this problem and saves equipment investment. At the same time, heating with vapor directly stripping can also control the residence time of the liquid by adjusting the amount of vapor to avoid overreaction. The invention simplifies the production process of furfural. The subsequent separation and purification of furfural is simple and easy. The whole process design is reasonable. The furfural yield is 10% to 30% higher and the unit energy consumption is 10% to 20% lower compared to the traditional one-step process.

BRIEF DESCRIPTION OF THE DRAWINGS

The following drawings of the present invention are hereby incorporated as part of the invention for the understanding of the invention. The embodiments and description of the invention have been presented in the drawings in order to explain the principles of the invention.

DETAILED DESCRIPTION

In the following description, numerous specific details are set forth in order to provide a more thorough understanding of the present invention. However, it would be apparent to those skilled in this art that the present invention may be implemented without one or more of these details. In other instances, some of the technical features well known in the art have not been described so as to not to confuse with the present invention.

Figure 1:
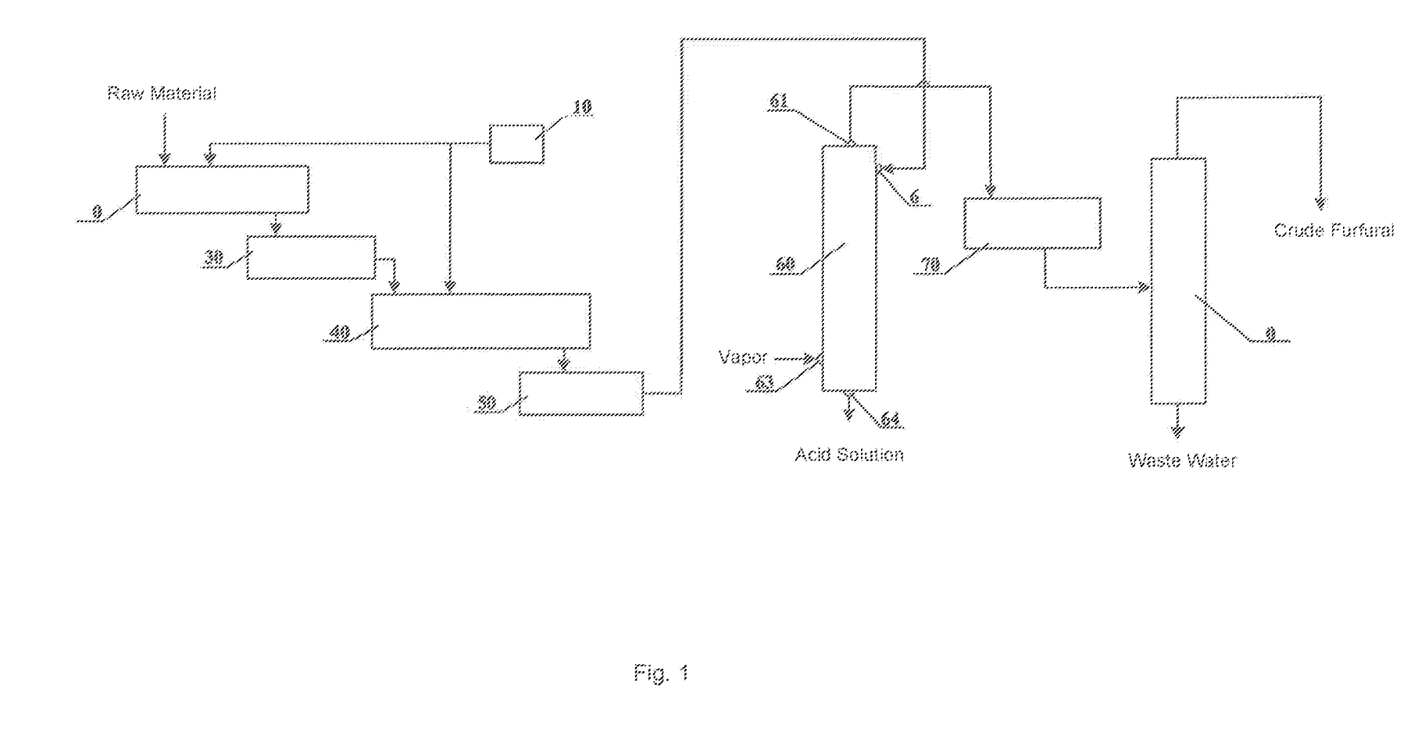
FIG. 1 is a schematic view of a system for continuously preparing furfural using lignocellulosic raw material according to an embodiment of the present invention.

FIG. 1 schematically illustrates an embodiment in accordance with the present invention.

As shown in FIG. 1, it is a system for continuously preparing furfural using lignocellulosic raw material, comprising an acid solution output unit 10, a raw material mixing unit 20, a feeding unit 30, a main reaction unit 40, a discharging unit 50, a stripping reaction column 60, a vapor outlet 61, a first raw material inlet 62, a stripping vapor inlet 63, an acid solution outlet 64, a separation unit 70, and a purification unit 80.

The system can continuously produce furfural using lignocellulosic raw material with the following process.

The lignocellulosic raw material is uniformly mixed with the first acid solution output from the acid solution output unit 10 in a certain ratio to form a mixture in the raw material mixing unit 20. The mixture is continuously fed to a feeding unit 30 which compresses the mixture and delivers the mixture outward. The mixture continuously and stably enters the main reaction unit 40, and is mixed with the second acid solution output from the acid solution output unit 10 at a pressure higher than the normal pressure to reach a set solid-liquid ratio to cause them to react. The resultant after completion of the reaction is continuously and stably conveyed to the discharging unit 50, and it is subject to solid-liquid separation in the discharging unit 50. The liquid output is an acid-containing pentose solution. The acid-containing pentose solution as heated by a heater to a first temperature enters the stripping reaction column 60 from the first raw material inlet 62 at the top of the stripping reaction column 60, and a stripping vapor of a second temperature enters the stripping reaction column 60 from the stripping vapor inlet 63 at the bottom of the stripping reaction column 60. The acid-containing pentose solution is subject to a dehydration/cyclization reaction in the stripping reaction column 60 to generate furfural, with the acid as a catalyst. Subsequently, the generated furfural is extracted from the vapor outlet 61 at the top of the stripping reaction column 60, and the acid solution is extracted from the acid solution outlet 64 at the bottom of the stripping reaction column 60. The extracted furfural-containing vapor enters the separation unit 70 connected to the stripping reaction column 60, and the acid in the furfural-containing vapor is neutralized in the separation unit 70 to obtain a furfural-containing vapor with a reduced acid content. The furfural-containing vapor with a reduced acid content enters the purification unit 80 connected to the separation unit 70 and is purified in the purification unit 80.

According to a preferred embodiment, the raw material mixing unit 20 may comprise a screw mixer for uniformly mixing the raw material and the first acid solution with spiral agitation to form a mixture and providing a continuous feed of the mixture to the feeding unit 30. The use of the screw mixer allows the raw material to be uniformly mixed well with the acid solution to ensure a smooth subsequent hydrolysis reaction.

According to a preferred embodiment, the feeding unit 30 may comprise a screw feeder with compression function. Preferably, the screw feeder comprises a compression section, and the inner diameter and the screw pitch of the compression section become smaller and smaller in the feeding direction, and more preferably the screw feeder comprises a plug section being located after the compression section and with the inner diameter and the screw pitch unchanged. The screw feeder is used to compress the mixture and deliver the mixture to the main reaction unit 40. The hydrolysis reaction in the main reaction unit 40 is carried out under a pressure higher than a normal pressure. The screw feeder of the feeding unit 30 can ensure that the material in the main reaction unit 40 will not go back into the feeding unit 30 and maintain the pressure stable in the main reaction unit 40, which ensures the hydrolysis reaction in the main reaction unit 40 to be carried out under a stable pressure. In addition, by using the screw feeder, continuous and stable feeding can also be provided without clogging.

According to a preferred embodiment, the feeding unit 30 may further comprise a first tapered discharging tube connected to the raw material mixing unit 20 and the screw feeder respectively for receiving the mixture from the raw material mixing unit 20 and conveying it to screw feeder. The use of the first tapered discharging tube for receiving and conveying the mixture in the feeding unit 30 can ensure that the mixture smoothly enters the screw feeder, thereby avoiding clogging or poor delivery resulted from poor fluidity of the uniform mixture output from the raw material mixing unit 20.

According to a preferred embodiment, the main body reaction unit 40 may comprise a screw reactor which is of a plug flow type and with no compression function. The mixture is subject to a hydrolysis reaction in the screw reactor of the main reaction unit 40. When the screw reactor is set to be of a plug flow, the reaction can be complete and the reaction efficiency can be improved, so that the solid-liquid mixing ratio of the mixture in the reactor can be consistent in any reaction stage, and the efficiency of the hydrolysis reaction is improved.

According to a preferred embodiment, the main reaction unit 40 may further comprise a second tapered discharging tube connected to the feeding unit 30 for receiving the mixture. On top of the second tapered discharging tube is further provided an acid solution adding means connected to the acid solution output unit 10 for adding the second acid solution. The use of the second tapered discharging tube for receiving and conveying the mixture in the main reaction unit 40 can ensure that the mixture smoothly enters the screw reactor, which avoids clogging or poor delivery resulted from poor fluidity of the solid-liquid mixture output from the feeding unit 30. The acid solution adding means arranged at the top of the second tapered discharging tube further supplements the acid solution required for the reaction to achieve a set solid-liquid ratio, so that the hydrolysis reaction can be efficiently conducted.

According to a preferred embodiment, the acid solution adding means can add a second acid solution by spraying. The use of the spraying manner can spray the second acid solution more uniformly to the mixture from the feeding unit 30 and facilitate uniform mixing of the second acid solution and the mixture.

According to a preferred embodiment, the main reaction unit 40 may further comprise a vapor input port for receiving high-temperature vapor. This vapor input can maintain the reaction temperature of the main reaction unit 40 in an appropriate range, and avoid a decrease in the reaction rate caused by the temperature drop.

According to a preferred embodiment, the main reaction unit 40 may further comprise a vent valve to discharge non-condensable gas generated during the reaction. In this way, it is possible to ensure that the pressure in the main reaction unit 40 is within a suitable range, thereby allowing the hydrolysis reaction to proceed stably.

According to a preferred embodiment, the temperature and pressure of the main reaction unit 40 can be adjusted and set by, for example, adjusting the temperature and pressure of the feeding, and controlling the vent valve, etc. The main reaction unit 40 can be set to have a temperature of 100° C. to 200° C. and a pressure of 0.1 MPa to 1.8 MPa, preferably a temperature of 100° C. to 160° C. and a pressure of 0.1 MPa to 0.8 MPa, more preferably a temperature of 115° C. to 125° C. and a pressure of 0.15 MPa to 0.25 MPa, and most preferably a temperature of 120° C. and a pressure of 0.2 MPa.

According to a preferred embodiment, the discharging unit 50 may comprise a screw discharger with compression function for extruding filtration and solid-liquid separation of the resultant. Preferably, the screw discharger comprises a compression section, of which the inner diameter and screw pitch become smaller and smaller along the discharging direction, and more preferably, the screw discharger further comprises a plug section being located after the compression section and with the inner diameter and the screw pitch unchanged. More preferably, there is a screen mesh at the wall of the screw discharger which discharges liquid through the screen mesh, and has a solid discharging port at the end for discharging solids. The screw discharger of the discharging unit 50 can ensure that the spraying will not happen during the process of outputting the resultant, maintain the pressure stable in the main reaction unit 40, and provide continuous and stable discharging without clogging.

According to a preferred embodiment, the temperature of the first acid solution is preferably 40° C. to 95° C., more preferably 55° C. to 65° C., most preferably 60° C.; the temperature of the second acid solution is preferably 110° C. to 200° C., more preferably 125° C. to 135° C., most preferably 130° C. Any acid concentration capable of achieving hydrolysis of lignocellulose falls into the scope of the present invention. According to a preferred embodiment, the first acid solution and/or the second acid solution may have an acid concentration of 0.1% to 10% by weight.

According to a preferred embodiment, the second acid solution added to the main reaction unit 40 is also capable of bringing the solid-liquid mixture to a set solid-liquid mass ratio, preferably a solid-liquid mass ratio of 1:3 to 1:8.

According to a preferred embodiment, the temperature and pressure in the raw material mixing unit 20 and the feeding unit 30 can be adjusted and set by, for example, adjusting the temperature and pressure of the feeding. The raw material mixing unit 20 can be set to have a temperature of 40° C. to 90° C. and a normal pressure; the feeding unit 30 can be set to have a temperature of 40° C. to 90° C.

According to a preferred embodiment, the first acid solution may be the acid solution extracted from the acid solution outlet, and so is the second acid solution. The cyclic utilization of the acid solution can reduce treatment cost thereof and environmental pollution.

According to a preferred embodiment, the separation unit 70 may further comprise a filtration device, preferably a ceramic filter, for filtering the furfural-containing vapor with a reduced acid content to further remove impurities from the furfural-containing vapor. The use of the filtration device can effectively reduce the amount of furfural mud generated in the subsequent furfural refining process and prolong the service life of the reboiler and heat exchange unit of the preliminary distillation column.

According to a preferred embodiment, the system for preparing furfural may further comprise a heat exchange unit comprising: a raw material passage and a furfural passage. The raw material passage receives the acid-containing pentose solution as a raw material, and the furfural passage receives the furfural-containing vapor from the separation unit 70. The acid-containing pentose solution and the furfural-containing vapor pass through the raw material passage and the furfural passage, respectively. The passages are separated from each other but enable the heat exchange between the acid-containing pentose solution and the furfural-containing vapor. The acid-containing pentose solution and the furfural solution as obtained after heat exchange are respectively delivered to the stripping reaction column 60 and the purification unit 80. The heat exchange unit can effectively utilize the heat of the furfural-containing vapor to increase the temperature of the acid-containing pentose solution, so that the acid-containing pentose solution can reach the reaction temperature faster and heat waste is avoided.

According to a preferred embodiment, the purification unit 80 may comprise a preliminary distillation column having a preliminary distillation column feed port at the middle, a preliminary distillation column vapor outlet and an aqueous phase liquid inlet at the top, and a reboiler vapor inlet and a preliminary distillation column bottom liquid outlet at the bottom; and a furfural solution heat exchanger, wherein the furfural solution is cooled to a third temperature by the furfural solution heat exchanger and enters the preliminary distillation column through the preliminary distillation column feed port. A preliminary distillation column reboiler is provided at the bottom of the preliminary distillation column, and a reflux unit is provided at the top of the column. The reflux unit comprises a preliminary distillation column condenser and a preliminary distillation column liquid separation tank. After exchanging heat through the preliminary distillation column reboiler, a part of the bottom liquid becomes reboiler vapor and returns to the preliminary distillation column via the reboiler vapor inlet. The preliminary distillation column condenser is connected to the preliminary distillation column vapor outlet for condensing the purified furfural-containing vapor to a condensate of a fourth temperature. The preliminary distillation column liquid separation tank is connected to the preliminary distillation column condenser for receiving the condensate, performing liquid separation to obtain an aqueous phase liquid and an oil phase liquid, returning the aqueous phase liquid to the preliminary distillation column through the aqueous liquid inlet, and outputting the oil phase liquid as a crude furfural product.

According to a preferred embodiment, the separation unit 70 may comprise an alkaline solution inlet to input an alkali solution for neutralization to neutralize the acid in the furfural-containing vapor, thereby preventing the acid from decomposing or polycondensing the furfural in a subsequent treatment.

According to a preferred embodiment, the separation method of the separation unit 70 may be one or more of inertial separation, filtration separation, and centrifugal separation. The present invention preferably employs a cyclone separator belonging to a centrifugal separation method for separating salt and solid impurities from the furfural-containing vapor to provide a furfural-containing vapor with a reduced acid content. The cyclone separator has the advantages of simple structure, convenient operation, high temperature resistance and long service life.

According to a preferred embodiment, the furfural preparing system may also comprise an acid solution heat exchanger for receiving the acid solution extracted from the acid solution outlet 64 at the bottom of the stripping reaction column 60 and conducting heat recovery.

According to a preferred embodiment, the purification unit 80 may further comprise a refining unit for performing refining of the crude furfural product by dehydration and removal of light components to obtain a product furfural.

According to a preferred embodiment, the purification unit 80 may further comprise a wastewater evaporator for evaporating and reusing a portion of the liquid discharged from the bottom of the preliminary distillation column.

According to a preferred embodiment, the first temperature may be set to be 80° C. to 155° C., and the second temperature may be set to be 150° C. to 220° C. The stripping reaction column 60 may be set to have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column 60 can be adjusted and set by adjusting the temperature and pressure of the feeding.

According to a preferred embodiment, the third temperature may be set to be 20° C. to 100° C., and the fourth temperature may be set to be 30° C. to 90° C. The preliminary distillation column may be set to have a temperature of 100° C. to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column can be adjusted and set by adjusting the temperature and pressure of the feeding, the reboiling ratio, and the reflux ratio, and the like.

According to a preferred embodiment, the bottom of the stripping reaction column 60 is free of a reboiler, and the top thereof is free of a reflux unit.

Figure 2:
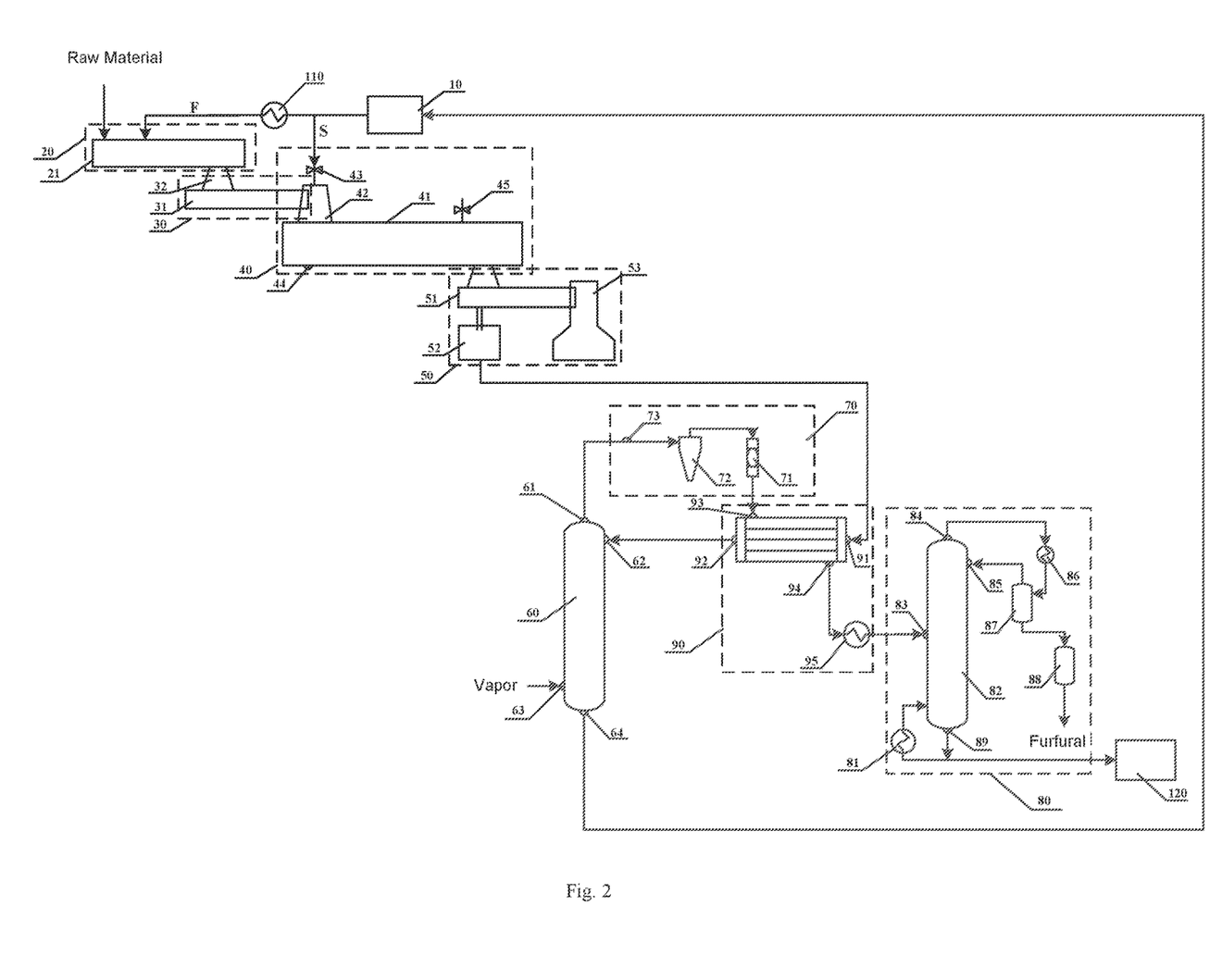
FIG. 2 is a schematic view of a system for continuously preparing furfural using lignocellulosic raw material according to another embodiment of the present invention.

FIG. 2 schematically illustrates a preferred embodiment in accordance with the present invention. Wherein, there is provided a system for continuously preparing furfural using lignocellulosic raw material, comprising an acid solution output unit 10, a raw material mixing unit 20, a screw mixer 21, a feeding unit 30, a screw feeder 31, a first tapered discharging tube 32, a main reaction unit 40, a screw reactor 41, a second tapered discharging tube 42, an acid solution adding means 43, a vapor input port 44, a vent valve 45, a discharging unit 50, a screw discharger 51, a sugar liquid collection tank 52, and a residue tank 53, a stripping reaction column 60, a vapor outlet 61, a first raw material inlet 62, a stripping vapor inlet 63, an acid solution outlet 64, a separation unit 70, a ceramic filter 71, a cyclone separator 72, an alkaline solution input port 73, a purification unit 80, a preliminary distillation column reboiler 81, a preliminary distillation column 82, a preliminary distillation column feed port 83, a preliminary distillation column vapor outlet 84, an aqueous phase liquid inlet 85, a preliminary distillation column condenser 86, a preliminary distillation column liquid separation tank 87, a refining unit 88, a preliminary distillation column bottom liquid outlet 89, a heat exchange unit 90, a second raw material inlet 91, a raw material outlet 92, a furfural inlet 93, a furfural outlet 94, a furfural solution heat exchanger 95, an acid solution heat exchanger 110, and a wastewater evaporator 120.

The device can continuously produce furfural with the following process.

The lignocellulosic raw material is continuously fed to the raw material mixing unit 20, wherein the raw material mixing unit 20 comprises a screw mixer 21 in which the raw material is uniformly mixed with the first acid solution from the acid solution output unit 10 (as shown by the arrow F) in a certain ratio to form a mixture, and the mixture is continuously output.

The uniformly mixed solid-liquid mixture enters the feeding unit 30, which includes the screw feeder 31 and the first tapered discharging tube 32. The mixture continuously enters the screw feeder 31 through the first tapered discharging tube 32. The screw feeder 31 has a compression function and includes a compression section and a plug section. The inner diameter and the screw pitch of the compression section become smaller and smaller along the feeding direction. The plug section is located after the compression section, and the inner diameter and the screw pitch remain unchanged. The screw feeder compresses the solid-liquid mixture and delivers it to the main reaction unit 40.

The main reaction unit 40 comprises a screw reactor 41, a second tapered discharging tube 42, an acid solution adding means 43, a vapor input port 44, and a vent valve 45. The mixture from the screw feeder 31 is fed into the second tapered discharging tube 42. The mixture continues to be mixed, in the second tapered discharging tube 42, with the second acid solution (as indicated by the arrow S) as added by the acid solution adding means 43 arranged at the top of the second tapered discharging tube 42 (preferably by spray addition) from the acid solution output unit 10, to reach the set solid-liquid ratio and then enters the screw reactor 41, and it is thoroughly stirred and mixed under a pressure higher than the normal pressure to carry out the reaction. The screw reactor 41 is preferably of a plug flow type and with no compression function. The second acid solution with high temperature can provide the heat as required for the reaction.

The vapor input port 44 can input vapor to the screw reactor 41 to compensate for heat loss. During the reaction, the vent valve 45 can be opened according to the pressure change in the screw reactor 41 to release the non-condensable gas and ensure the stable pressure of the system.

The resultant after completion of the reaction enters the discharging unit 50. The discharging unit 50 comprises a screw discharger 51 with compression function, a sugar liquid collection tank 52, and a residue tank 53. The screw discharger 51 comprises a compression section and a plug section. The inner diameter and the screw pitch of the compression section become smaller and smaller along the discharging direction. The plug section is located after the compression section, and the inner diameter and screw pitch remain unchanged. The resultant is subject to solid-liquid separation with the extrusion of the screw discharger 51. There is a screen mesh at the wall of the screw discharger which discharges the liquid through the screen mesh, and the liquid is an acid-containing pentose solution and enters the sugar liquid collection tank 52. A solid discharging port at the end of the screw discharger is used for discharging solids, and the solids enter the residue tank 53.

A stripping vapor of a second temperature enters the column from the stripping vapor inlet 63 at the bottom of the stripping reaction column 60, and the acid-containing pentose solution of the first temperature enters the column from the first raw material inlet 62 at the top of the stripping reaction column 60. The acid-containing pentose solution is subject to a dehydration/cyclization reaction in the stripping reaction column 60 to generate furfural, with the acid as a catalyst. Subsequently, the generated furfural is extracted from the vapor outlet 61 at the top of the stripping reaction column 60, and the acid solution is extracted from the acid solution outlet 64 at the bottom of the stripping reaction column 60. A portion of the extracted acid solution is subject to heat exchange through the acid solution heat exchanger 110 for heat recovery and is then delivered to the screw mixer 21 as the first acid solution, and the remaining portions as the second acid solution are directly delivered to the acid solution adding means 43, for supplementing the acid solution and providing heat.

The extracted furfural-containing vapor enters the separation unit 70 connected to the stripping reaction column 60. The alkali liquid enters the separation unit 70 from the alkaline solution input port 73 to neutralize the acid in the furfural-containing vapor, and the vapor then enters the cyclone separator 72 to separate the salt obtained by neutralization from the furfural-containing vapor to generate a furfural-containing vapor with a reduced acid content. The furfural-containing vapor with the reduced acid content then passes through the ceramic filter 71 to further remove impurities in the vapor, thereby preventing the vapor from coking in the subsequent heat exchange process and reducing the production of furfural mud.

The furfural-containing vapor enters the heat exchange unit 90 through the furfural inlet 93, and the acid-containing pentose solution enters the heat exchange unit 90 through the second raw material inlet 91. The acid-containing pentose solution and the furfural-containing vapor pass through the raw material passage and the furfural passage, respectively. The passages are separated from each other but enable the heat exchange between the acid-containing pentose solution and the furfural-containing vapor. The acid-containing pentose solution after heat exchange enters the stripping reaction column 60 through the first raw material inlet 62 after being output from the raw material outlet 92. The furfural solution obtained after heat exchange is output from the furfural outlet 94.

The furfural solution then enters the purification unit 80 connected to the separation unit 70. First, the furfural solution is cooled to a third temperature through the furfural solution heat exchanger 95 and then enters the preliminary distillation column 82 from the preliminary distillation column feed port 83, and the purified furfural-containing vapor is extracted from the preliminary distillation column vapor outlet 84 at the top of the column after the furfural solution is purified in the preliminary distillation column 82. Subsequently, the purified furfural-containing vapor enters the preliminary distillation column condenser 86 to be cooled to a fourth temperature and is then delivered to the preliminary distillation column liquid separation tank 87 in which an aqueous phase liquid and an oil phase liquid are obtained from liquid separation. The aqueous phase liquid flows back to the preliminary distillation column 82 through the aqueous liquid inlet 85, and the oil phase liquid is output as the crude furfural product. A portion of the bottom liquid extracted from the preliminary distillation column bottom liquid outlet 89 becomes reboiler vapor after heat exchange with the primary distillation column reboiler 81 and returns to the preliminary distillation column 82 through the reboiler vapor inlet, and the remaining portions of the bottom liquid are extracted as wastewater.

According to a preferred embodiment, the purification unit 80 may further comprise a refining unit 88 for performing refining of the crude furfural product by dehydration and removal of light components of so as to obtain a product furfural.

According to a preferred embodiment, the system may also comprise a wastewater evaporator 120 for evaporating and reusing a portion of the bottom liquid of the preliminary distillation column 82.

According to a preferred embodiment, the first temperature may be set to be 80° C. to 155° C., and the second temperature may be set to be 150° C. to 220° C. The stripping reaction column 60 may be set to have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column 60 can be adjusted and set by adjusting the temperature and pressure of the feeding.

According to a preferred embodiment, the third temperature may be set to be 20° C. to 100° C., and the fourth temperature may be set to be 30° C. to 90° C. The preliminary distillation column 82 may be set to have a temperature of 100° C. to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column 82 can be adjusted and set by adjusting the temperature and pressure of the feeding, the reboil ratio, and the reflux ratio, and the like.

The present invention also relates to a method for continuously preparing furfural using lignocellulosic raw material, the method comprising: an acid solution output step for outputting a first acid solution and a second acid solution respectively; a raw material mixing step for mixing the raw material with the first acid solution to form a mixture; a feeding step for compressing the mixture and conveying the mixture outward; a hydrolysis reaction step for uniformly mixing the mixture with the second acid solution and causing them to perform a hydrolysis reaction at a pressure higher than a normal pressure; a discharging step for performing solid-liquid separation of a resultant obtained from the hydrolysis reaction, in order to obtain a liquid as an acid-containing pentose solution; a stripping reaction step, which is performed using a stripping reaction column, wherein the acid-containing pentose solution from the discharging step of a first temperature enters the stripping reaction column from the top; a stripping vapor of a second temperature enters the stripping reaction column from the bottom; the stripping vapor is in countercurrent contact with the pentose solution, which is subject to a dehydration/cyclization reaction so as to obtain a furfural-containing vapor and an acid solution; a separation step, wherein the furfural-containing vapor is neutralized and the resulting salt is separated from the furfural-containing vapor to provide a furfural-containing vapor with a reduced acid content; and a purification step, wherein the resulting furfural is purified.

According to a preferred embodiment, the raw material and the first acid solution may be uniformly mixed by a screw mixer in the raw material mixing step.

According to a preferred embodiment, the mixture may be compressed and conveyed by a screw feeder with compression function in the feeding step.

According to a preferred embodiment, the mixture may enter the screw feeder through a first tapered discharging tube.

According to a preferred embodiment, a screw reactor of a plug flow type and with no compression function may be used in the hydrolysis reaction step.

According to a preferred embodiment, the mixture may enter the screw reactor through a second tapered discharging tube, and an acid solution adding means may be further provided at the top of the second tapered discharging tube for adding the second acid solution.

According to a preferred embodiment, the acid solution adding means may add the second acid solution by spraying.

According to a preferred embodiment, the high-temperature vapor may be input through the vapor input port in the hydrolysis reaction step.

According to a preferred embodiment, the non-condensable gas generated during the hydrolysis reaction can be discharged through the vent valve in the hydrolysis reaction step.

According to a preferred embodiment, the hydrolysis reaction step may be carried out at a temperature of 100° C. to 200° C. and a pressure of 0.1 MPa to 1.8 MPa.

According to a preferred embodiment, the product is subject to extruding filtration and solid-liquid separation using a screw discharger with compression function in the discharging step.

According to a preferred embodiment, the temperature of the first acid solution is 40° C. to 95° C.; the temperature of the second acid solution is 110° C. to 200° C.; the acid concentration of the first acid solution and the second acid solution is 0.1% to 10% by weight.

According to a preferred embodiment, the main reaction unit has a reaction temperature of 100° C. to 200° C. and a reaction pressure of 0.1 MPa to 1.8 MPa, which can be set by, for example, adjusting the temperature and pressure of the feeding, and controlling the vent valve, and the like.

According to a preferred embodiment, the raw material mixing step may be carried out at a temperature of 40° C. to 90° C. and a normal pressure, and the feeding step may be carried out at a temperature of 40° C. to 90° C., which can be set by, for example, adjusting the temperature and pressure of the feeding.

According to a preferred embodiment, the first acid solution and/or the second acid solution may be an acid solution obtained from the stripping reaction step.

According to a preferred embodiment, the screw feeder may comprise a compression section, of which the inner diameter and the screw pitch become smaller and smaller along a feeding direction.

According to a preferred embodiment, the screw feeder may further comprise a plug section being located after the compression section and with its inner diameter and screw pitch unchanged.

According to a preferred embodiment, the screw discharger may comprise a compression section, of which the inner diameter and the screw pitch become smaller and smaller along a discharging direction.

According to a preferred embodiment, the screw discharger may further comprise a plug section being located after the compression section and with its inner diameter and screw pitch unchanged.

According to a preferred embodiment, there may be a screen mesh at the wall of the screw discharger, which discharges liquid through the screen mesh and has a solid discharging port at the end for discharging solids.

According to a preferred embodiment, the separation step may further comprise filtering the furfural-containing vapor with a reduced acid content to provide a filtered furfural-containing vapor.

According to a preferred embodiment, the method may further comprise a heat exchange step, wherein the furfural-containing vapor from the separation step performs an isolated heat exchange with the acid-containing pentose solution with a temperature lower than the first temperature, so that the acid-containing pentose solution reaches the first temperature as a raw material for the stripping reaction step to provide a furfural solution.

According to a preferred embodiment, the purification step comprises rectification with a preliminary distillation column. The furfural solution is cooled to a third temperature and enters the preliminary distillation column for rectification. The purified furfural-containing vapor obtained from rectification is condensed to a fourth temperature and separated. The obtained aqueous phase liquid returns to the preliminary distillation column, and the oil phase liquid is output as a crude furfural product. A portion of the liquid at the bottom of the column obtained from the rectification exits the preliminary distillation column and reenters therein as reboiler vapor after exchanging heat with the preliminary distillation column reboiler.

According to a preferred embodiment, the furfural-containing vapor may be neutralized with an alkaline solution in the separation step.

According to a preferred embodiment, the salt may be separated from the furfural-containing vapor using a cyclone separator in the separation step to provide a furfural-containing vapor with a reduced acid content.

According to a preferred embodiment, the acid solution obtained from the stripping reaction step is subject to heat recovery.

According to a preferred embodiment, the method may further comprise a refining step, wherein the crude furfural product is subject to refining by dehydration and removal of light components to obtain a product furfural.

According to a preferred embodiment, the method may further comprise evaporating and reusing a portion of the bottom liquid of the column exiting the preliminary distillation column.

According to a preferred embodiment, the first temperature may be 80° C. to 155° C. The second temperature may be 150° C. to 220° C. The stripping reaction column may have a temperature of 140° C. to 210° C. at the top and a temperature of 150° C. to 220° C. at the bottom, and have a pressure of 0.26 MPa to 2.2 MPa (gauge pressure) at the top and a pressure of 0.37 MPa to 2.2 MPa (gauge pressure) at the bottom. The temperature and pressure of the stripping reaction column may be adjusted and set by adjusting the temperature and pressure of the feeding.

According to a preferred embodiment, the third temperature may be 20° C. to 100° C. The fourth temperature may be 30° C. to 90° C. The preliminary distillation column may have a temperature of 100° C. to 115° C. at the top and a temperature of 120° C. to 160° C. at the bottom, and have a pressure of 0 MPa to 0.03 MPa (gauge pressure) at the top and a pressure of 0 MPa to 0.35 MPa (gauge pressure) at the bottom. The temperature and pressure of the preliminary distillation column may be adjusted and set by adjusting the temperature and pressure of the feeding, the reboil ratio, the reflux ratio, and the like.

According to a preferred embodiment, the bottom of the stripping reaction column is free of a reboiler, and the top thereof is free of a reflux unit.

According to a preferred embodiment, the acid may be selected from at least one of sulphur acid, hydrochloric acid, phosphoric acid or nitric acid, and the acid may have a concentration of 0.1% to 10% by weight, preferably 1% to 5% by weight, most preferably 2% to 4% by weight.

According to a preferred embodiment, the pentose solution may have a sugar concentration of 1 g/l to 100 g/l, preferably 1 g/l to 50 g/l, most preferably 5 g/l to 30 g/l.

The above method of the present invention can be carried out by using the system of the present invention or a system with other configurations as long as the effects of the invention can be achieved.

EXAMPLE

The system as shown in FIG. 2 is used to continuously prepare furfural using lignocellulosic raw material.

The lignocellulosic raw material is continuously fed to the raw material mixing unit 20, wherein the raw material mixing unit 20 comprises a screw mixer 21 in which the raw material is uniformly mixed with the first acid solution (as shown by the arrow F) in a certain ratio to form a mixture, and the mixture is continuously output. The first acid solution is a portion of the acid solution at the bottom of the stripping reaction column 60, and is cooled to 60° C. through heat exchange with the acid solution heat exchanger 110.

The uniformly mixed solid-liquid mixture enters the feeding unit 30, which includes the screw feeder 31 and the first tapered discharging tube 32. The mixture continuously enters the screw feeder 31 through the first tapered discharging tube 32. The screw feeder 31 has a compression function and includes a compression section and a plug section. The inner diameter and the screw pitch of the compression section become smaller and smaller along the feeding direction. The plug section is located after the compression section, and the inner diameter and the screw pitch remain unchanged. The screw feeder 31 compresses the solid-liquid mixture and delivers it to the main reaction unit 40 outward.

The main reaction unit 40 comprises a screw reactor 41, a second tapered discharging tube 42, an acid solution adding means 43, a vapor input port 44, and a vent valve 45. The mixture from the screw feeder 31 is fed into the second tapered discharging tube 42. The mixture continues to be mixed, in the second tapered discharging tube 42, to reach the set solid-liquid ratio, with the second acid solution (as indicated by the arrow S). The second acid solution is a portion of the acid solution at the bottom of the stripping reaction column 60, which is added by the acid solution adding means 43 arranged at the top of the second tapered discharging tube 42 (preferably by spray addition), and then enters the screw reactor 41 after solid-liquid mixing, and it is thoroughly stirred and mixed under a pressure higher than the normal pressure to carry out the reaction. The screw reactor 41 is preferably of a plug flow type and with no compression function. The second acid solution does not undergo heat exchange and cooling, and the solution with high temperature can provide the temperature as required for the reaction.

The vapor input port 44 can input vapor to the screw reactor 41 to compensate for heat loss. During the reaction, the vent valve 45 can be opened according to the pressure change in the screw reactor 41 to release the non-condensable gas and ensure the stable pressure of the system.

The product after completion of the reaction enters the discharging unit 50. The discharging unit 50 comprises a screw discharger 51 with compression function, a sugar liquid collection tank 52, and a residue tank 53. The screw discharger 51 comprises a compression section and a plug section. The inner diameter and the screw pitch of the compression section become smaller and smaller along the discharging direction. The plug section is located after the compression section, and its inner diameter and screw pitch remain unchanged. The resultant is subject to solid-liquid separation with the extrusion of the screw discharger 51. The filtered solid material continuously enters the residue tank 53 for further processing. After the filtered acid-containing pentose solution is collected by the collection tank 52, it exchanges heat in the heat exchange unit 90 with the filtered furfural-containing vapor recovered from the top of the stripping reaction column 60. The acid-containing pentose solution enters the stripping reaction column 60 through the first raw material inlet 62 after being preheated to 150° C. The stripping vapor with a temperature of 180° C. is fed from the stripping vapor inlet 63 into the stripping reaction column 60. The ascending stripping vapor is brought into countercurrent contact with the pentose solution. The acid-containing pentose solution is subject to the dehydration/cyclization reaction in the reaction column after being further heated to 170° C. in the stripping reaction column 60. The generated furfural enters the stripping vapor and is extracted out from the vapor outlet 61 at the top of the stripping reaction column 60 at 170° C. (with a pressure of 0.74 MPa at the top), and the extracted furfural-containing vapor contains 8% by weight of furfural.

The extracted furfural-containing vapor is output to the separation unit 70 and subject to vapor phase neutralization with a 12% by weight of sodium carbonate solution. The resulting salt is separated from the furfural-containing vapor by a cyclone separator 22 so as to obtain a furfural-containing vapor with a reduced acid content. The furfural-containing vapor then enters the ceramic filter 71, is filtered and then enters the heat exchange unit 90.

In the heat exchange unit 90, the filtered furfural-containing vapor is subject to heat exchange with the acid-containing pentose solution to obtain a furfural solution with a temperature of 170° C.

The furfural solution enters the purification unit 80, and after being further cooled to 85° C. by the furfural solution heat exchanger 95, it then enters the preliminary distillation column 82 from the preliminary distillation column feed port 83. After purification, the crude furfural vapor is extracted from the preliminary distillation column vapor outlet 84, and enters the preliminary distillation column liquid separation tank 87 after being condensed to 80° C. by the preliminary distillation column condenser 86. The aqueous phase liquid and the oil phase liquid are obtained by liquid separation, wherein the aqueous phase liquid contains an aldehyde concentration of 6% by weight, and the oil phase liquid contains 8% by weight of water.

The aqueous phase liquid returns from the top of the preliminary distillation column liquid separation tank 87 and enters the preliminary distillation column 82 from the aqueous phase liquid inlet 85. The oil phase liquid is output as a crude furfural product and enters a crude furfural storage tank.

The crude furfural product can be used as a product furfural after subsequent refining by dehydration and removal of light components. The furfural yield is 88% (relative to the theoretical yield of a pentose solution of 5 g/l).

The acid solution extracted from the acid solution outlet 64 at the bottom of the stripping reaction column 60 has a temperature of 175° C. A portion of the extracted acid solution is subject to heat exchange through the acid solution heat exchanger 110 for heat recovery and is then delivered to the screw mixer 21 as the first acid solution, and the remaining portions as the second acid solution are directly delivered to the acid solution adding means 43, for supplementing the acid solution and providing heat. The preliminary distillation column reboiler 80 is heated by vapor. A portion of the bottom liquid extracted from the preliminary distillation column bottom liquid outlet 89 becomes reboiler vapor after heat exchange with the preliminary distillation column reboiler 31, and returns to the preliminary distillation column 32 via the reboiler vapor inlet. The remaining portions of the bottom liquid are extracted as wastewater. The extracted wastewater can enter the wastewater evaporator 120 and be recycled after secondary evaporation.

The present invention has been described by the above embodiments, but it is to be understood that the foregoing embodiments are only for the purpose of illustration and description but are not intended to limit the invention within the scope of the embodiments as described. In addition, those skilled in the art should understand that the present invention is not limited to the above embodiments. Many variations and modifications can still be made according to the teachings of the present invention. These variations and modifications fall within the scope of the present invention as defined by the appended claims and their equivalents.

What is claimed is:

1. A system for continuously preparing furfural using lignocellulosic raw material, wherein the system comprises:
   an acid solution output unit, the acid solution output configured to output a first acid solution and a second acid solution, respectively;
   a raw material mixing unit connected to the acid solution output unit, the raw material mixing unit configured to mix the lignocellulosic raw material with the first acid solution so as to form a first mixture, the raw material mixing unit further configured to continuously output the first mixture;

a feeding unit connected to the raw material mixing unit, the feeding unit configured to receive the first mixture, compress the first mixture and output the first mixture;

a main reaction unit connected to the feeding unit and the acid solution output unit, the a main reaction unit configured to receive the first mixture and the second acid solution respectively, and sufficiently stir and mix the first mixture with the second acid solution under a pressure higher than a normal pressure in such a way that the first mixture reacts with the second acid solution so as to produces a second mixture;

a discharging unit connected to the main reaction unit, the discharging unit configured to perform solid-liquid separation of the second mixture and output an acid-containing pentose solution;

a stripping reaction column comprising, a vapor outlet formed at a top portion of the stripping reaction column, a first raw material inlet formed at the top portion of the stripping reaction column, a stripping vapor inlet formed at a bottom portion of the stripping reaction column, and an acid solution outlet formed at the bottom of the stripping reaction column; wherein the first raw material inlet is configured to receive an acid-containing pentose solution of a first temperature from the discharging unit as a raw material so as to perform a dehydration/cyclization reaction, wherein the stripping vapor inlet is configured to receive a stripping vapor of a second temperature, wherein the vapor outlet is configured to supply a furfural-containing vapor obtained from the dehydration/cyclization reaction, and wherein the acid solution outlet is configured to extract an acid solution from the bottom of the column;

a separation unit connected to the vapor outlet, the separation unit configured to neutralize an acid in the furfural-containing vapor and separate the resulting salt from the furfural-containing vapor so as to provide a furfural-containing vapor with a reduced acid content; and a purification unit connected to the separation unit, the purification unit configured to purify the furfural-containing vapor.

2. The system according to claim 1, wherein the raw material mixing unit comprises a screw mixer configured to uniformly mix the raw material and the first acid solution with spiral agitator, wherein the uniform mixture is continuously fed to the feeding unit.

3. The system according to claim 1, wherein the feeding unit comprises a screw feeder, the screw feeder configured to compress the first mixture, and
wherein the feeding unit comprises a first tapered discharging tube connected to the raw material mixing unit and the screw feeder respectively, the feeding unit configured to receive the mixture from the raw material mixing unit and convey the mixture to the screw feeder.

4. The system according to claim 1, wherein the main reaction unit comprises a screw reactor with no compression function, and
wherein the main reaction unit comprises a second tapered discharging tube connected to the feeding unit and for receiving the mixture, and on top of the second tapered discharging tube is further provided with an acid solution adding means connected to the acid solution output unit, for adding the second acid solution.

5. The system according to claim 4, wherein the acid solution adding means adds the second acid solution by spraying.

6. The system according to claim 1, wherein the main reaction unit further comprises a vapor input port for receiving high-temperature vapor,
wherein the main reaction unit further comprises a vent valve for discharging non-condensable gas generated during the reaction, and
wherein the main reaction unit is configured to operate at a temperature between 100° C. to 200° C. and a pressure between 0.1 MPa to 1.8 MPa.

7. The system according to claim 1, wherein the discharging unit comprises a screw discharger with compression function, the screw discharger configured to perform extruding filtration and solid-liquid separation of the second mixture.

8. The system according to claim 7, wherein the screw discharger comprises a compression section, the compression section configured to have an inner diameter that gradually decreases along a discharging direction, the compression section configured to have a screw pitch that gradually decreases along a discharging direction,
wherein the screw discharger further comprises a plug section, the plug section formed after the compression section, the plug section configured to have a constant inner diameter and screw pitch, and
wherein the screw discharger is configured to have a screen mesh at the wall of the screw discharger, wherein the screen mesh is configured to discharge liquid through the screen mesh and have a solid discharging port at the end for discharging solids.

9. The system according to claim 1, wherein at least one of the following apply:
the temperature of the first acid solution is between 40° C. to 95° C.; the temperature of the second acid solution is between 110° C. to 200° C.; the acid concentration of the first acid solution and the second acid solution is between 0.1% to 10% by weight,
the main reaction unit is configured to have a temperature between 100° C. to 200° C. and have a pressure between 0.1 MPa between 1.8 MPa,
the raw material mixing unit is configured to have a temperature between 40° C. to 90° C. and a normal pressure, and the feeding unit is configured to have a temperature between 40° C. to 90° C.,
the first acid solution is an acid solution extracted from the acid solution outlet,
the second acid solution is an acid solution extracted from the acid solution outlet,
the separation unit comprises an alkaline solution input port for inputting an alkaline solution to neutralize the acids in a furfural-containing vapor,
the separation unit comprises a cyclone separator for separating the salt from the furfural-containing vapor to provide a furfural-containing vapor with a reduced acid content,
the system further comprises an acid solution heat exchanger for receiving an acid solution flowing from the acid solution outlet and performing heat recovery,
the stripping reaction column is configured to have a top pressure between 0.26 MPa to 2.2 MPa (gauge pressure) and a bottom pressure between 0.37 MPa to 2.2 MPa (gauge pressure), the bottom of the stripping reaction column is free of a reboiler, and the top thereof is free of a reflux unit, and the first temperature is configured to be between 80° C. to 155° C.; the second temperature is configured to be between 150° C. to 220° C.; the stripping reaction column top temperature is configured to be between 140° C. to 210° C. and the stripping reaction column bottom temperature is configured to be between 150° C. to 220° C.

10. The system according to claim 3, wherein the screw feeder includes a compression section, the compression section configured to have an inner diameter that gradually decreases along a feeding direction, the compression section configured to have a screw pitch that gradually decreases along a feeding direction, and
wherein the screw feeder further comprises a plug section, the plug section formed after the compression section, the plug section configured to have a constant inner diameter and screw pitch.

11. The system according to claim 1, wherein the separation unit further comprises a filtration unit for filtering the furfural-containing vapor with a reduced acid content so as to provide a filtered furfural-containing vapor.

12. The system according to claim 1, wherein the system further comprises a heat exchange unit comprising:
a raw material passage including a second raw material inlet for receiving an acid-containing pentose solution with a temperature lower than the first temperature; and a raw material outlet connected to the first raw material inlet, for providing an acid-containing pentose solution of the first temperature to the stripping reaction column, and
a furfural passage, the furfural passage configured to be isolated from the raw material passage, the furfural passage configured to perform heat exchange, the furfural passage configured to include a furfural inlet connected to the separation unit and a furfural outlet connected to the purification unit, the furfural inlet configured to receive the furfural-containing vapor from the separation unit; and the furfural outlet configured to provide a furfural solution.

13. The system according to claim 12, wherein the purification unit comprises:
a preliminary distillation column having a preliminary distillation column feed port at the middle, a preliminary distillation column vapor outlet and an aqueous phase liquid inlet at the top, a reboiler vapor inlet and a preliminary distillation column bottom liquid outlet at the bottom;
a furfural solution heat exchanger, the furfural solution heat exchanger configured to cool the furfural solution to a third temperature before entering the preliminary distillation column via the preliminary distillation column feed port;
wherein a preliminary distillation column reboiler is formed at a bottom portion of the preliminary distillation column, and a reflux unit is provided at a top portion of the preliminary distillation column, the reflux unit including a preliminary distillation column condenser and a preliminary distillation column liquid separation tank;
wherein the preliminary distillation column reboiler is configured to allow a portion of the bottom liquid of the column to form as a reboiler vapor through heat exchange and return the reboiler vapor to the preliminary distillation column through the reboiler vapor inlet;
wherein the preliminary distillation column condenser is connected to the preliminary distillation column vapor outlet, and the preliminary distillation column condenser is configured to condense the purified furfural-containing vapor to a condensate of a fourth temperature;
the preliminary distillation column liquid separation tank is connected to the preliminary distillation column condenser, and the preliminary distillation column liquid separation tank is configured to receive the condensate, perform liquid separation so as to obtain an aqueous phase liquid and an oil phase liquid, and return the aqueous phase liquid to the preliminary distillation column through the aqueous phase liquid inlet and output the oil phase liquid as a crude furfural product.

14. The system according to claim 13, wherein at least one of the following apply:
the purification unit further comprises a refining unit for performing refining of the crude furfural product by dehydration and removal of light components so as to obtain a product furfural,
the system further comprises a wastewater vaporizer connected to the preliminary distillation column bottom liquid outlet, the wastewater vaporizer configured to evaporate and reuse the remaining bottom liquid from the preliminary distillation column bottom liquid outlet,
the third temperature is configured to be between 20° C. to 100° C.; the fourth temperature is configured to be between 30° C. to 90° C.; the preliminary distillation column top temperature is configured to be between 100° C. to 115° C. and the preliminary distillation column bottom temperature is configured to be between 120° C. to 160° C., and
the preliminary distillation column top pressure is configured to be between 0 MPa to 0.03 MPa (gauge pressure) and the preliminary distillation column bottom pressure is configured to be between 0 MPa to 0.35 MPa (gauge pressure).

15. A method for continuously preparing furfural using lignocellulosic raw material, the method comprising:
an acid solution output step for outputting a first acid solution and a second acid solution respectively;
a raw material mixing step for mixing the lignocellulosic raw material with the first acid solution so as to form a first mixture;
a feeding step for compressing the mixture and conveying the mixture outward;
a hydrolysis reaction step for uniformly mixing the mixture with the second acid solution and performing a hydrolysis reaction at a pressure higher than a normal pressure;
a discharging step for performing solid-liquid separation of a second mixture obtained from the hydrolysis reaction, so as to obtain a liquid as an acid-containing pentose solution;
a stripping reaction step is performed at a stripping reaction column, wherein the acid-containing pentose solution from the discharging step of a first temperature enters the stripping reaction column from the top; wherein a stripping vapor of a second temperature enters the stripping reaction column from the bottom; wherein the stripping vapor is in countercurrent contact with the pentose solution, wherein the pentose solution is subject to a dehydration/cyclization reaction so as to obtain a furfural-containing vapor and an acid solution;

a separation step for neutralizing the furfural-containing vapor and separating the resulting salt from the furfural-containing vapor so as to provide a furfural-containing vapor with a reduced acid content; and
purification step for purifying, the furfural-containing vapor.

16. The method according to claim 15, wherein at least one of the following apply:
the raw material and the first acid solution are uniformly mixed by a screw mixer in the raw material mixing step,
the furfural-containing vapor is neutralized with an alkaline solution in the separation step,
the salt is separated from the furfural-containing vapor using a cyclone separator in the separation step to provide a furfural-containing vapor with a reduced acid content,
the acid solution obtained from the stripping reaction step is subject to heat recovery,
the first temperature is configured to be between 80° C. to 155° C.; the second temperature is configured to be between 150° C. to 220° C.; the stripping reaction column top temperature is configured to be between 140° C. to 210° C. and the stripping reaction column bottom temperature is configured to be between 150° C. to 220° C.,
the stripping reaction column top pressure is configured to be between 0.26 MPa to 2.2 MPa (gauge pressure) and the stripping reaction column bottom pressure is configured to be between 0.37 MPa to 2.2 MPa (gauge pressure),
the bottom of the stripping reaction column is free of a reboiler, and the top thereof is free of a reflux unit,
the acid is selected from at least one of sulphur acid, hydrochloric acid, phosphoric acid or nitric acid, and the acid has a concentration between 0.1% to 10% by weight, and
the pentose solution has a sugar concentration between 1 g/l to 100 g/l.

17. The method according to claim 15, wherein the first mixture is compressed and conveyed by a screw feeder with compression function in the feeding step, and
wherein the first mixture enters the screw feeder through a first tapered discharging tube.

18. The method according to claim 15, wherein a screw reactor with no compression function is used in the hydrolysis reaction step,
wherein the first mixture enters the screw reactor through a second tapered discharging tube, and an acid solution adding means is further provided at the top of the second tapered discharging tube for adding the second acid solution, and
wherein the acid solution adding means adds the second acid solution by spraying.

19. The method according to claim 15, wherein at least one of the following apply:
a high-temperature vapor is input through a vapor input port in the hydrolysis reaction step,
a non-condensable gas generated during the hydrolysis reaction is discharged through a vent valve in the hydrolysis reaction step, and
the hydrolysis reaction step is carried out at a temperature between 100° C. to 200° C. and a pressure between 0.1 MPa to 1.8 MPa.

20. The method according to claim 15, wherein the second mixture is subject to extruding filtration and solid-liquid separation using a screw discharger with compression function in the discharging step.

21. The method according to claim 15, wherein at least one of the following apply:
the temperature of the first acid solution is between 40 to 95° C.; the temperature of the second acid solution is between 110° C. to 200° C.; the acid concentration of the first acid solution and the second acid solution is between 0.1% to 10% by weight,
the main reaction unit has a reaction temperature configured to be between 100° C. to 200° C. and a reaction pressure configured to be between 0.1 MPa to 1.8 MPa,
the raw material mixing step is carried out at a temperature configured to be between 40° C. to 90° C. and under a normal pressure, and the feeding step is carried out at a temperature configured to be between 40° C. to 90° C.,
the first acid solution is an acid solution obtained from the stripping reaction step, and
the second acid solution is an acid solution obtained from the stripping reaction step.

22. The method according to claim 17, wherein the screw feeder comprises a compression section, the compression section configured to have an inner diameter that gradually decreases along a feeding direction, the compression section configured to have a screw pitch that gradually decreases along a feeding direction.

23. The method according to claim 22, wherein the screw feeder further comprises a plug section, the plug section formed after the compression section, the plug section configured to have a constant inner diameter and screw pitch.

24. The method according to claim 20, wherein the screw discharger comprises a compression section, the compression section configured to have an inner diameter that gradually decreases along a discharging direction, the compression section configured to have a screw pitch that gradually decreases along a discharging direction.

25. The method according to claim 24, wherein the screw discharger further comprises a plug section, the plug section formed after the compression section, the plug section configured to have a constant inner diameter and screw pitch.

26. The method according to claim 20, wherein the screw discharger is configured to have a screen mesh at the wall of the screw discharger, the screen mesh configured to discharge liquid through the screen mesh, the screen mesh configured to have a solid discharging port at the end for discharging solids.

27. The method according to claim 15, wherein the separation step further comprises filtering the furfural-containing vapor with a reduced acid content to provide a filtered furfural-containing vapor,
wherein the method further comprises a heat exchange step, wherein the furfural-containing vapor from the separation step performs an isolated heat exchange with the acid-containing pentose solution with a temperature lower than the first temperature such that the acid-containing pentose solution reaches the first temperature as a raw material for the stripping reaction step, and a furfural solution is provided, and
wherein the purification step comprises rectification with a preliminary distillation column; wherein the furfural solution is cooled to a third temperature through heat exchange and enters the preliminary distillation column for rectification; the purified furfural-containing vapor obtained from rectification is condensed to a fourth temperature and separated; an aqueous phase liquid obtained from liquid separation is returned to the preliminary distillation column, and an oil phase liquid obtained from liquid separation is output as a crude furfural product; a portion of the bottom liquid obtained from the rectification exits the preliminary distillation column and reenters therein as reboiler vapor after exchanging heat with a preliminary distillation column reboiler.

28. The method according to claim 27, wherein one or more of at least one of the following apply:
the purification step further comprises a refining step, wherein the crude furfural product is subject to refining by dehydration and removal of light components to obtain a product furfural,
the purification step further comprises evaporating and reusing the remaining portions of the bottom liquid exiting the preliminary distillation column,
the third temperature is configured to be between 20° C. to 100° C.; the fourth temperature is configured to be between 30° C. to 90° C.; the preliminary distillation column top temperature is 100° C. to 115° C. and the preliminary distillation column bottom temperature is configured to be between 120° C. to 160° C., and
the preliminary distillation column top pressure is configured to be between 0 MPa to 0.03 MPa (gauge pressure) and the preliminary distillation column bottom pressure is configured to be between 0 MPa to 0.35 MPa (gauge pressure).

29. The method according to claim 16, wherein the acid has a concentration between 1% to 5% by weight.

30. The method according to claim 16, wherein the acid has a concentration between 2% to 4% by weight.

31. The method according to claim 16, wherein the pentose solution has a sugar concentration between 1 g/l to 50 g/l.

32. The method according to claim 16, wherein the pentose solution has a sugar concentration between 5 g/l to 30 g/l.

* * * * *

UNITED STATES PATENT AND TRADEMARK OFFICE
CERTIFICATE OF CORRECTION

Page 1 of 1

PATENT NO. : 11,767,304 B2
APPLICATION NO. : 16/894672
DATED : September 26, 2023
INVENTOR(S) : Xu et al.

It is certified that error appears in the above-identified patent and that said Letters Patent is hereby corrected as shown below:

On the Title Page

Item (73) Assignee, Please change "Eco Environmental Energy Research Institute Limited" to --Eco BiomassTechnology Company Limited--.

Signed and Sealed this
Nineteenth Day of December, 2023

Katherine Kelly Vidal
*Director of the United States Patent and Trademark Office*